(12) United States Patent
Wang et al.

(10) Patent No.: US 7,604,804 B2
(45) Date of Patent: Oct. 20, 2009

(54) ENHANCING ANTI-HIV EFFICIENCY THROUGH MULTIVALENT INHIBITORS TARGETING OLIGOMERIC GP120

(75) Inventors: Lai-Xi Wang, Ellicott City, MD (US); Hengguang Li, Lutherville, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 402 days.

(21) Appl. No.: 11/054,398

(22) Filed: Feb. 9, 2005

(65) Prior Publication Data

US 2005/0176642 A1    Aug. 11, 2005

Related U.S. Application Data

(60) Provisional application No. 60/542,916, filed on Feb. 9, 2004, provisional application No. 60/548,059, filed on Feb. 26, 2004.

(51) Int. Cl.
*A61K 39/385* (2006.01)
*A61K 39/12* (2006.01)
*A61K 39/21* (2006.01)

(52) U.S. Cl. ............ 424/184.1; 424/193.1; 424/196.11; 424/204.1; 424/207.1; 424/208.1

(58) Field of Classification Search .............. 424/194.1; 503/402, 408
See application file for complete search history.

(56) References Cited

U.S. PATENT DOCUMENTS 6,139,843 A    10/2000    Rubinstein et al.

FOREIGN PATENT DOCUMENTS

EP    0 891 982 A2    1/1999
EP    0 719 281 B1    8/1999

OTHER PUBLICATIONS

Shinya et al. In vivo delivery of therapeutic proteins by genetically-modified cells: comparison of organoids and human serum albumin alginate-coated beads 1999. Biomedical and Pharmacotherapy vol. 53, pp. 471-483.*
BM[PEO]2(1,8-bis-Maleimidodiethyleneglycol) [online]. Pierce Biotechnology, Inc, 2002 [retrieved on Nov. 16, 2005]. Retrieved from the Internet: <URL: https://www.piercenet.com/products/browse.cfm?fldID=02030209>.*
Lalezari et al. A Controlled Phase II trial assessing three doses of enfuvirtide in combination with abacavir . . . 2003. Antiviral Therapy vol. 8 No. 4, pp. 279-287.*
Wu et al. Dimeric association and segmental variability in the structure of human CD4. Nature May 29, 1997, vol. 387, p. 527-530.*
McInerney et al. Mutation-Directed Chemical Cross-Linking of Human Immunodeficiency Virus Type 1 gp41 Oligomers. Journal of Virology, Feb. 1998, vol. 72, No. 2, pp. 1523-1533.*
Green et al. Quantitative evaluation of the lengths of homobifunctional protein cross-linking reagents used as molecular rulers. Protein Science 2001, vol. 10, pp. 1293-1304.*
Tsunehiro et al. Enzyme coupled immunoassay of insulin using a novel coupling reagent. Journal of Biochemistry 1976. vol. 79, pp. 233-236.*
Richman, D.D., (2001) HIV chemotherapy. *Nature 410*, 995-1001.
Chan, D.C., et al., (1998) HIV entry and its inhibition. *Cell 93*, 681-684.
Kwong, P.D., et al., (1998) Structure of an HIV gp120 envelope glycoprotein in complex with the CD4 receptor and a neutralizing human antibody. *Nature 393*, 648-659.
Wyatt, R., et al., (1998) The antigenic structure of the HIV gp120 envelope glycoprotein. *Nature 393*, 705-711.
Smith, D.H., et al., (1987) Blocking of HIV-1 infectivity by a soluble, secreted form of the CD4 antigen.*Science 238*, 1704-1707.
Deen, K.C., et al., (1988) A soluble form of CD4 (T4) protein inhibits AIDS virus infection. *Nature 331*, 82-84.
Traunecker, A., et al., (1988) Soluble CD4 molecules neutralize human immunodeficiency virus type 1. *Nature 331*, 84-86.
Burton, D.R., et al., (1994) Efficient neutralization of primary isolates of HIV-1 by a recombinant human monoclonal antibody. *Science 266*, 1024-1027.
Saphire, E.O., et al., (2001) Crystal structure of a neutralizing human IGG against HIV-1: a template for vaccine design. *Science 293*, 1155-1159.
Martin, L., et al., (2000) Engineering novel bioactive mini-proteins on natural scaffolds. *Tetrahedron 56*, 9451-9460.
Vita, C., et al., (1999) Rational engineering of a miniprotein that reproduces the core of the CD4 site interacting with HIV-1 envelope glycoprotein. *Proc. Natl. Acad. Sci. USA 96*, 13091-13096.
Martin, L., et al., (2003) Rational design of a CD4 mimic that inhibits HIV-1 entry and exposes cryptic neutralization epitopes. *Nat. Biotechnol. 21*, 71-76.
Sanders, R.W., et al., (2002) Stabilization of the soluble, cleaved, trimeric form of the envelope glycoprotein complex of human immunodeficiency virus type 1. *J. Virol. 76*, 8875-8889.
Schulke, N., et al., (2002) Oligomeric and conformational properties of a proteolytically mature, disulfide-stabilized human immunodeficiency virus type 1 gp140 envelope glycoprotein. *J. Virol. 76*, 7760-7776.
Salzwedel, K., et al., (2000) Cooperative subunit interactions within the oligomeric envelope glycoprotein of HIV-1: functional complementation of specific defects in gp120 and gp41. *Proc. Natl. Acad. Sci. U S A 97*, 12794-12799.
Kwong, P.D., et al., (2000) Oligomeric modeling and electrostatic analysis of the gp120 envelope glycoprotein of human immunodeficiency virus. *J. Virol. 74*, 1961-1972.

(Continued)

*Primary Examiner*—Larry R Helms
*Assistant Examiner*—Louise Humphrey
(74) *Attorney, Agent, or Firm*—Marianne Fuierer; Moore & Van Allen PLLC

(57) ABSTRACT

The present invention relates to multivalent HIV inhibitors that bind to multiple sites on a trimeric gp120 complex thereby blocking the CD4 binding site on the trimeric gp120 complex and inhibiting the attachment and entry of HIV through gp120-CD4 interactions.

21 Claims, 7 Drawing Sheets

OTHER PUBLICATIONS

Staropoli, I., et al., (2000) Processing, stability, and receptor binding properties of oligomeric envelope glycoprotein from a primary HIV-1 isolate. *J. Biol. Chem. 275*, 35137-35145.

Zhu, P., et al., (2003) Electron tomography analysis of envelope glycoprotein trimers on HIV and simian immunodeficiency virus virions. *Proc. Natl. Acad. Sci. USA 100*, 15812-15817.

Mammen, M., et al., (1998) Polyvalent interactions in biological systems: Implications for design and use of multivalent ligands and inhibitors. *Angew. Chem. Int. Ed. 37*, 2754-2794.

Kitov, P.I., et al., (2003) Optimization of tether length in nonglycosidically linked bivalent ligands that target sites 2 and 1 of a Shiga-like toxin. *J. Am. Chem. Soc. 125*, 3284-3294.

Dekker, F.J., et al., (2002) Replacement of the intervening amino acid sequence of a Syk-binding diphosphopeptide by a nonpeptide spacer with preservation of high affinity. *Chembiochem 3*, 238-242.

Kitov, P.I., et al., (2000) Shiga-like toxins are neutralized by tailored multivalent carbohydrate ligands. *Nature 403*, 669-672.

Fan, E., et al., (2000) High-affinity pentavalent ligands of *E. coli* heat-labile enterotoxin by modular structure-based design. *J. Am. Chem. Soc. 122*, 2663-2664.

Kiessling, L.L., et al., (2000) Synthetic multivalent ligands in the exploration of cell-surface interactions. *Curr. Opin. Chem. Biol. 4*, 696-703.

Wang, L.X., et al., (2003) Carbohydrate-centered maleimide cluster as new types of templates for multivalent peptide assembling: Synthesis of multivalent HIV-1 gp41 peptides. *Bioorg. Med. Chem. 11*, 129-136.

Willey, R.L., et al., (1988) In vitro mutagenesis identifies a region within the envelope gene of the human immunodeficiency virus that is critical for infectivity. *J. Virol. 62*, 139-147.

Wu, Z., et al., (2003) From pro defensins to defensins: synthesis and characterization of human neutrophil pro alpha-defensin-1 and its mature domain. *J. Pept. Res. 62*, 53-62.

Li, et al., (2004) Synthetic Bivalent CD4-Mimetic Miniproteins Show Enhanced Anti-HIV Activity over the Monovalent Miniprotein, *Bioconjugate Chem.15*, 783-789.

* cited by examiner

ENHANCING ANTI-HIV EFFICIENCY THROUGH MULTIVALENT INHIBITORS TARGETING OLIGOMERIC GP120

CROSS-REFERENCE TO RELATED APPLICATIONS

This application claims priority from U.S. Provisional Patent Application Nos. 60/542,916 and 60/548,059 filed on Feb. 9, 2004 and Feb. 26, 2004, respectively, in the names of Lai-Xi Wang and Hengguang Li for "ENHANCING ANTI-HIV EFFICIENCY THROUGH MULTIVALENT INHIBITORS TARGETING OLIGOMERIC GP120" the content of which are incorporated by reference herein for all purposes.

STATEMENT OF GOVERNMENT RIGHTS

The United States Government has rights in this invention under National Institute of Heath Grant Nos. A151235 and A154354.

BACKGROUND OF THE INVENTION

1. Field of Invention

The present invention relates to antiviral agents, and more particularly, to multivalent antiviral agents that bind to trimeric gp120 complexes thereby blocking the CD4 binding site on the gp120 complexes and inhibiting the attachment and entry of HIV through gp120-CD4 interactions.

2. Description of the Related Art

The human immunodeficiency virus (HIV) has been implicated as the primary cause of the slowly degenerative immune system disease termed acquired immune deficiency syndrome (AIDS). In humans, HIV replication occurs prominently in CD4 T lymphocyte populations, and HIV infection leads to depletion of this cell type and eventually to immune incompetence, opportunistic infections, neurological dysfunctions, neoplastic growth, and ultimately death.

The HIV viral particle comprises a viral core, composed in part of capsid proteins, together with the viral RNA genome and those enzymes required for early replicative events. Myristylated gag protein forms an outer shell around the viral core, which is, in turn, surrounded by a lipid membrane envelope derived from the infected cell membrane. The HIV envelope surface glycoproteins are synthesized as a single 160 kilodalton precursor protein, which is cleaved by a cellular protease during viral budding into two glycoproteins, gp41 and gp120. gp41 is a transmembrane glycoprotein and gp120 is an extracellular glycoprotein, which remains noncovalently associated with gp41, in a trimeric or multimeric form. Data from recent structural and biochemical studies have demonstrated that the HIV-1 envelope glycoprotein gp120 is displayed as a gp41-associated trimer and forms envelope spikes on the surface of HIV virions (14-18). Recent electron tomography further confirmed this theory (19).

It is known that the initial step of HIV entry is characterized by the interaction of HIV-1 envelope glycoprotein gp120 with host receptor CD4. The CD4 binding site on gp120 is centered on a conserved, hydrophobic pocket denoted the "Phe43 cavity." It has been demonstrated that molecules targeting the conserved CD4-binding pocket, such as soluble CD4, CD4 mimetic proteins and HIV-neutralizing antibody b12, are potent inhibitors against HIV infection (6-13).

Although considerable effort has been expended on the design of effective therapeutics, currently no curative anti-retroviral drugs against AIDS exist. The new treatment regimens for HIV-1 include a combination of anti-HIV compounds, which target reverse transcriptase (RT), such as azidothymidine (AZT), lamivudine (3TC), dideoxyinosine (ddl), tenofovir, nevirapine, efavirenz, or anti-HIV compounds which target HIV protease such as saquinavir, nelfinavir, indinavir, amprenavir, and lopinavir. Unfortunately, the development of viral resistance occurs in a significant number of treated patients using these compounds. This combined with the development of anti-retroviral drug induced toxicity continues to limit the overall impact of current available treatments.

Thus, the toxicity and emergency of drug-resistant viruses associated with current drug regimen prompts development of new drugs that act with a different mode of action and with improved anti-HIV potency. Accordingly, there is a need for new drugs that blocks HIV attachment and entry at the stage of HIV envelope binding to host receptor CD4.

SUMMARY OF INVENTION

The present invention provides for improved compositions and vaccines that include multivalent HIV inhibitors capable of simultaneously occupying two or more of the CD4-binding cavities (Phe43 cavities) in a trimeric gp120 complex and bind to the envelope spikes more tightly thereby effectively blocking HIV attachment and entry.

In one aspect, the present invention relates to a multivalent HIV inhibitor molecule that comprises at least two gp120 binding molecules that target the CD4 binding pocket on a trimeric HIV gp120 complex and wherein the gp120 binding molecules are separated by a spacer/linker molecule of sufficient length to provide for binding of the gp120 binding molecules to the CD-4 binding sites on trimeric gp120 sites on the surface of the virion. Preferably, the distance between the reactive sites on the gp120 binding molecules when attached to the spacer/linker is in the range between 30 to 60 Å, and more preferably in the range between 50 to 55 Å. The reactive sites are those areas of the gp120 binding molecules that bind to the "Phe43 cavity" on gp120.

Generally, the spacer/linker of the present invention may include any molecule that can bind at least two of the gp120 binding molecules at a sufficient distance to allow each of the gp120 binding molecules to bind to a "Phe43 cavity" of gp120. The spacer/linker may be cleavable or noncleavable, however preferably, the spacer/linker is noncleavable under physiological conditions and at a pH of from about 6.8 to about 7.5. The spacer/linker may include amino acid residues having a sufficient number to provide for a sequence that meets the distance requirements between the adjacent "Phe43 cavities" of adjacent gp120. Further the spacer/linker may include, but is not limited, to the following trivalent and bivalent molecules, such as tris(2-carboxyethyl)phosphine hydrochloride; tris-succinimidyl aminotriacetate; tris-(2-maleimidoethyl)amine; 5, 5'-Dithio-bis-(2-nitobenzoic acid); bis-[β-(4-zaidosalicylamido)ethyl]disulfide; 1,4-bis-maleimidobutane; 1,4-bis-maleimidyl-2,3-dihydroxybutane; bis-maleimidohexane; bis-maleimidoethane; 1,8-bis-maleimidotriethyleneglycol; 1,8-bis-(6-maleimidocaproylamido)-triethyleneglycol; 1,8-bis-[6-(4-N-maleimidomethyl-cyclohexane-1-carboxyl)amido]caproxyl-triethyleneglycol; 1,11-bis-maleimidotetraethyleneglycol; bis[2-(Succinimidyloxycarbonyloxy)-ethyl]sulfone; bis[Sulfosuccinimidyl] suberate; disuccinimidyl glutarate; dithiobis(succinimidyl propionate); disuccinimidyl suberate; dithio-bis-maleimidoethane; 3,3-dithiobis(sulfosuccinimidyl propionate); dthylene glycol bis(sulfosuccinimidylsuccinate); and dimethyl pimelimidate 2HCl Relevant spacer/linker structures may include the following trivalent and bivalent templates:

Y = CH$_2$, O, NH, S

R = [maleimide], [acetate ester with X leaving group], NH$_2$, CHO, N$_3$

X = I, Br, Cl n = 1-50, and any other numbers

Z = CH, N, [cyclen], [cyclam-like], Cyclodextrin, [oval], or other cores

Peptide rings

Y = CH$_2$, O, NH, S, or any other link structures such as cyclic structures

R = [maleimide], [acetate ester with X leaving group], NH$_2$, CHO, N$_3$, or other functional groups X = I, Br, Cl n = 1-50, and any other numbers In another aspect, the present invention relates to bi, tri and polyvalent HIV inhibitors comprising at least two monomeric units that target the CD4 binding pocket on the trimeric HIV gp120 complex, wherein the monomeric units may be the same or different. The monomeric units may include mimetic proteins such as CD4M9 (SEQ ID NO: 1), CD4M33 (SEQ ID NO: 2); synthesized compounds such as BMS378806, BMS488043 or any molecule that recognizes and targets for binding with the "Phe43 cavity" of gp120.

Advantageously the multivalent HIV inhibitors of the present invention bind specifically to the CD4 binding sites on HIV-1 gp120 before HIV entry and therefore use of these inhibitors in a drug composition will provide for specific binding to HIV virus. The bi, tri and polyvalent HIV inhibitors of the present invention may be used as an antiviral drug, topical microbicides or components for inclusion in an HIV vaccine.

In yet another aspect, the present invention relates to a pharmaceutical composition comprising the described multivalent HIV inhibitors and a pharmaceutically acceptable carrier. The compositions of the present invention may further comprise at least one additional antiviral agent. The additional antiviral agent may include any agent that inhibits entry into a cell or replication therein of the HIV viruses, including but not limited to nucleoside RT inhibitors, CCR5 inhibitors/antagonists, viral entry inhibitors and their functional analogs including nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Fuzeon (T-20), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies;

viral entry inhibitors, such as Fuzeon (T-20), NB-2, NB-64, T-649, T-1249, SCH-C, SCH-D, PRO 140, TAK 779, TAK-220, RANTES analogs, AK602, UK-427, 857; and functional analogs or equivalents thereof.

Still another aspect of the present invention relates to a method of inhibiting entry of HIV in a cell, the method comprising:

introducing an effective amount of a multivalent HIV inhibitor, wherein the multivalent HIV inhibitor comprises monomeric units that are linked by a linker/spacer and wherein the monomeric units bind to CD-4 binding sites on an oligomeric gp120. The monomeric units may include CD4M9, CD4M33, BMS 378806, BMS 488043 and similar small molecules that bind specifically to the CD4 binding sites located on the gp120 of the HIV virion.

Another aspect of the present invention relates to a method to reduce dependency and/or effective amount of an anti-reverse transcriptase or protease acting HIV antiviral agent by substituting the antiviral agent with a multivalent HIV inhibitor of the present invention. By substituting and/or augmenting antiviral agents with a multivalent HIV inhibitor of the present invention, antiretroviral ARV therapy may be discontinued, amounts of antiviral agents can be reduced at least temporarily, and the ARV therapy is deintensified and simplified.

Yet another aspect of the present invention provides for isolated and purified polynucleotides that encode for a multivalent HIV inhibitor of the present invention, wherein the multivalent HIV inhibitor comprises at least two mimetic proteins that bind to the "Phe43 cavity" on gp120 and an amino acid spacer/linker positioned between the mimetic proteins.

In another embodiment, the present invention contemplates peptide sequence modifications, such as minor variations, deletions, substitutions or derivitizations of the amino acid sequence of the sequences disclosed herein, so long as the peptide has substantially the same activity or function as the unmodified peptides. A modified peptide will retain activity or function associated with the unmodified peptide, the modified peptide will generally have an amino acid sequence "substantially homologous" with the amino acid sequence of the unmodified sequence.

In an alternative embodiment, the present invention provides an expression vector comprising a polynucleotide that encodes for a multivalent HIV inhibitor of the present invention, wherein the monomeric units are proteins and the spacer is an amino acid sequence.

In yet another embodiment, the present invention provides a recombinant host cell transfected with a polynucleotide that encodes for a multivalent HIV inhibitor of the present invention.

In still another embodiment, the present invention contemplates a process of preparing a multivalent HIV inhibitor peptide comprising:

transfecting a cell with a polynucleotide that encodes for at least two mimetic proteins that bind to the CD4 binding site of gp120 and an amino acid spacer positioned therebetween to produce a transformed host cell; and maintaining the transformed host cell under biological conditions sufficient for expression of the peptide.

Another aspect of the present invention relates to generating a multivalent HIV inhibitor for binding with a trimeric gp120 complex, the method comprising the steps of:

covalently linking or attaching at least two monomeric units to a linker/spacer thereby forming the multivalent HIV inhibitor.

The monomeric units that are linked by a spacer include molecules that target the CD4 binding site on the trimeric HIV gp120 complex, wherein the molecules may include the same or a different members selected from the group consisting of CD4M9, CD4M33, BMS-488043 and BMS378806. Preferably, the spacer is of sufficient length to provide for binding of the monomeric units to the site on the trimeric gp120 complex that directly interacts with a CD4 receptor on a T cell.

Other features and advantages of the invention will be apparent from the following detailed description, drawings and claims.

DETAILED DESCRIPTION OF THE INVENTION

Figure 1:
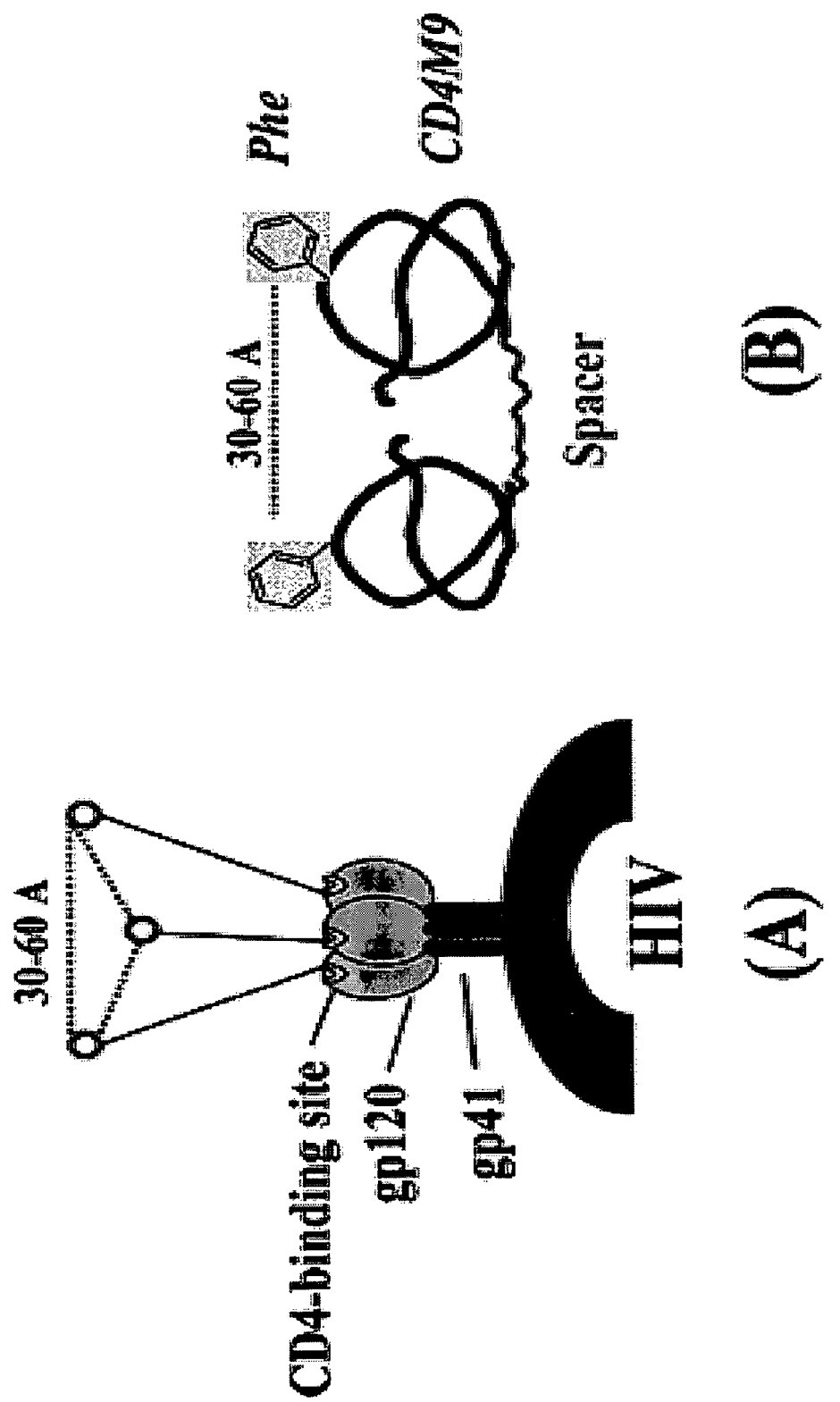
FIGS. 1A and B show the positioning of "Phe43 cavities" on the trimeric gp120 complex and estimated to be in the range of 30-55 Å (FIG. 1A) and a general structure of the designed bivalent inhibitors was shown in FIG. 1B.

In order to facilitate review of the various embodiments of the invention and provide an understanding of the various elements and constituents used in making and using the present invention, the following terms used in the invention description have the following meanings.

DEFINITIONS

The term "spacer/linker" as used herein refers to a molecule that connects the at least two monomeric units to form a multivalent HIV inhibitor. Particular examples of spacer/linkers may include an amino acid spacer that is of sufficient length of residues to place the monomeric units in an appropriate spatial position to match the CD4 binding sites on the trimeric gp120. The amino acid spacer can essentially be any length, for example, as few as 5 or as many as 200 or more amino acids. Other examples of applicable spacer/linkers include a molecule that meets the distance requirements between the adjacent "Phe43 cavity" of gp120, including but not limited to the following trivalent and bivalent molecules, such as tris(2-carboxyethyl)phosphine hydrochloride; tris-succinimidyl aminotriacetate; tris-(2-maleimidoethyl) amine; 5, 5'-Dithio-bis-(2-nitobenzoic acid); bis-[β-(4-zaidosalicylamido)ethyl]disulfide; 1,4-bis-maleimidobutane; 1,4-bis-maleimidyl-2,3-dihydroxybutane; bis-maleimidohexane; bis-maleimidoethane; 1, 8-bis-maleimidotriethyleneglycol; 1,11-bis-maleimidotetraethyleneglycol; bis[2-(Succinimidyloxycarbonyloxy)-ethyl]sulfone; bis[Sulfosuccinimidyl]suberate; disuccinimidyl glutarate; dithiobis(succinimidyl propionate); disuccinimidyl suberate; dithio-bis-maleimidoethane; 3,3-dithiobis(sulfosuccinimidyl propionate); dthylene glycol bis(sulfosuccinimidylsuccinate); and dimethyl pimelimidate 2HCl. Relevant structures may include the following trivalent and bivalent templates:

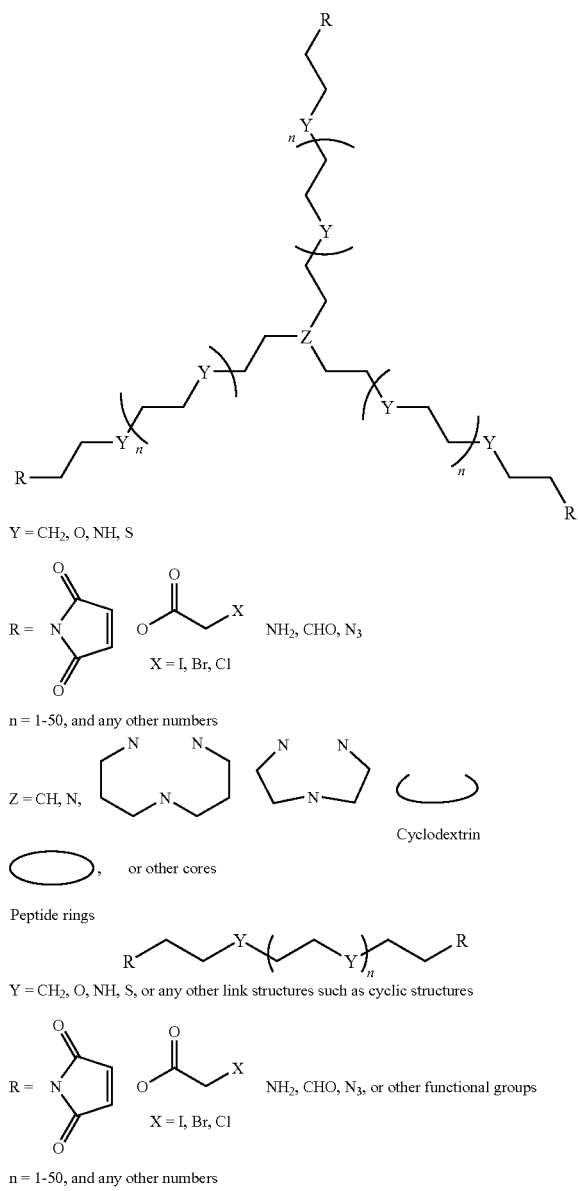

The terms "peptide," "polypeptide," "miniprotein" and "protein" as used herein are used interchangeably to denote a sequence polymer of at least two amino acids covalently linked by an amide bond.

The term "therapeutic," as used herein, means a treatment administered to a subject who exhibits signs of pathology for the purpose of diminishing or eliminating those signs.

The term "therapeutically effective amount," as used herein means an amount of compound that is sufficient to provide a beneficial effect to the subject to which the compound is administered. A beneficial effect means rendering a virus incompetent for replication, inhibition of viral replication, inhibition of infection of a further host cell, or increasing CD4 T-cell count, for example.

The Invention:

Multivalent HIV inhibitors

Recent progress in understanding of gp120 structure and receptor binding has provided insight into designing inhibitors that block the HIV-1 gp120-CD4 interactions. The HIV-1 envelope glycoproteins are displayed as oligomers, rather than a monomer, in both the virion and the infected cells. The functional units of envelope glycoproteins on both the virion and the infected cells are oligomeric gp120, i.e., envelope spikes, rather than a monomeric envelope glycoprotein species. Thus, the native oligomeric gp120 (envelope spikes) on virion or infected cells is actually a multivalent target containing multiple CD4 binding sites. As such, the native, oligomeric gp120 represents a typical multivalent target for multiple ligand binding.

Thus, an appropriate multivalent HIV inhibitor would be more effective for binding to the (multivalent) oligomeric gp120 complex than a monomeric inhibitor, such as presently used in almost all current CD4 binding site specific inhibitors. In the present invention the multivalent interaction, in which multiple receptors on one biological entity binds to multiple ligands on another entity simultaneously significantly enhance the affinity of a multivalent inhibitor of the present invention for the gp120 binding complex. Thus, through simultaneous multivalent interactions with multiple binding sites on the gp120 spikes of HIV-1, the devised multivalent HIV inhibitors are more effective in blocking HIV-1 infection, and are a novel class of anti-HIV drugs for the treatment of AIDS.

The present invention relates to a multivalent HIV inhibitor that is able to occupy two or more CD4 binding sites on the native gp120 spikes. Preferably, the multivalent HIV inhibitor comprises at least two molecules that mimic the CD4 epitope and are covalently bonded or attached to a linker at a sufficient distance from each other to bind to the CD4 binding sites on the native gp120 spikes.

The multivalent HIV inhibitors of the present invention may be administered as a composition with various pharmaceutically acceptable carriers. Pharmaceutically acceptable carriers include those approved for use in animals and humans and include diluents, adjuvants, excipients or any vehicle with which a compound, such as the multivalent CD4 mimetic species is administered. More specifically, pharmaceutically acceptable carriers include but are not limited to water, oils, saline, dextrose solutions, glycerol solutions, excipients such as starch, glucose, lactose, sucrose, gelatin, malt, rice, flour, chalk, silica gel, sodium stearate, glycerol monostearate, talc, sodium chloride, powdered non-fat milk, propylene glycol and ethanol. Pharmaceutical compositions may also include wetting or emulsifying agents, or pH buffering compounds.

In one embodiment, the present invention provides for compositions that include a multivalent HIV inhibitor comprising at least two gp120 binding molecules that inhibits attachment of the HIV virion to the CD4 receptor on the cell surface and optionally at least one additional antiviral agent, wherein the additional antiviral agent reduces replication of the HIV virus by a different mode of action. The compositions comprising a multivalent HIV inhibitor and optionally an additional antiviral agent, may be administered, separately, simultaneously, concurrently or consecutively.

The additional antiviral agent may include, but not limited to, nucleoside RT inhibitors, CCR5 inhibitors/antagonists, viral entry inhibitors and functional analogs thereof. Preferably, the antiviral agent comprises nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Fuzeon (T-20), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies;

viral entry inhibitors, such as Fuzeon (T-20), NB-2, NB-64, T-649, T-1249, SCH-C, SCH-D, PRO 140, TAK 779, TAK-220, RANTES analogs, AK602, UK-427, 857; and functional analogs thereof.

Methods for Preventing and/or Treating a Viral Infection

The compositions and methods of the present invention can be used to treat or reduce effects of HIV viral infection in a subject potentially exposed to the infection. At least one multivalent HIV inhibitor comprising at least two gp120 binding molecules that inhibit attachment of the HIV virion to the cell surface of the present invention may be administered for the treatment of HIV either as a single therapeutic agent or in combination with other antiretroviral drugs that attack the virus at different points of replication.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, such as sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables. Preferred carriers include neutral saline solutions buffered with phosphate, lactate, Tris, and the like.

The compositions of the invention are administered in substantially non-toxic dosage concentrations sufficient to ensure the release of a sufficient dosage unit of the present complexes into the patient to provide the desired inhibition of the HIV virus. The actual dosage administered will be determined by physical and physiological factors such as age, body weight, severity of condition, and/or clinical history of the patient. The active ingredients are ideally administered to achieve in vivo plasma concentrations of the multivalent HIV species of about 0.01 uM to about 100 uM, more preferably about 0.1 to 10 uM. It will be understood, however, that dosage levels that deviate from the ranges provided may also be suitable in the treatment of a given viral infection.

Therapeutic efficacy of the multivalent HIV inhibitor can be determined by standard pharmaceutical procedures in cell cultures or experimental animals, e.g., for determining The $LD_{50}$ (The Dose Lethal To 50% Of The Population) and The $ED_{50}$ (the dose therapeutically effective in 50% of the population). The dose ratio between toxic and therapeutic effects is the therapeutic index and it can be expressed as the ratio $LD_{50}/ED_{50}$. Compounds, which exhibit large therapeutic indexes, are preferred. The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Screening Assays

The present invention provides a process for detecting HIV infection in biological samples, wherein the process comprises reacting the biological samples comprising suspected HIV virus with the multivalent HIV inhibitor of the present invention to form a gp120/multivalent complex and detecting this complex.

A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample.

In accordance with a screening assay process, a biological sample is exposed to a multivalent HIV inhibitor of the present invention. Typically, the biological sample is exposed to the multivalent HIV inhibitor under biological reaction conditions and for a period of time sufficient for gp120/multivalent complexes to form. Biological reaction conditions include ionic composition and concentration, temperature, pH and the like. Ionic composition and concentration can range from that of distilled water to a 2 molal solution of NaCl. Temperature preferably is from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. Exposure time will vary inter alia with the biological conditions used, the concentration of the multivalent species and the nature of the sample (e.g., fluid or tissue sample). Means for determining exposure time are well known to one of ordinary skill in the art.

The presence of a gp120 in the biological sample is detected by detecting the formation of gp120/multivalent species complex. Means for detecting such complexes are well known in the art and include such procedures as centrifugation, affinity chromatography and the like, binding of an antibody to the gp120/multivalent species complex.

In one embodiment, detection is accomplished by detecting an indicator affixed to the antibody. Exemplary and well known indicators include radioactive labels (e.g., $^{32}P$, $^{125}I$, $^{14}C$), a second antibody or an enzyme such as horse radish peroxidase. Means for affixing indicators to bound antibodies are well known in the art and available in commercial kits.

Vaccines

The present invention further provides compositions comprising a therapeutically effective amount of a multivalent HIV inhibitor and administered for an extended period of time. Doses to be administered are variable according to the treatment period, frequency of administration, the host, and the nature and severity of the HIV infection. The dose can be determined by one of skilled in the art without an undue amount of experimentation.

The desired dose is preferably presented as two, three, four, five, six or more sub-doses administered at appropriate intervals throughout the day. These sub-doses may be administered in unit dosage forms, for example, containing 0.01 to 1000 mg, preferably 1 mg to 50 mg, depending on the number of sub-doses.

The therapeutic compositions according to the present invention may be employed in combination with other-therapeutic agents for the treatment of viral infections or conditions. Examples of such further therapeutic agents include agents that are effective for the treatment of viral infections or associated conditions such as immunomodulatory agents such as thymosin, ribonucleotide reductase inhibitors such as 2-acetylpyridine 5-[(2-chloroanilino) thiocarbonyl) thiocarbonohydrazone, interferons such as alpha-interferon, 1-beta-D-arabinofuranosyl-5-(1-propynyl)uracil, 3'-azido-3'-deoxythymidine, ribavirin and phosphonoformic acid.

Routes of Administration

The compositions according to the present invention, may be administered for therapy by any suitable route including oral, rectal, nasal, topical (including transdermal, buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

The formulations may conveniently be presented in unit dosage form and may be prepared by methods known in the art of pharmacy. In general, the formulations are prepared by uniformly and intimately bringing into association the separate ingredients with liquid carriers or finely divided solid carriers or both, and then if necessary shaping the product.

Compositions suitable for transdermal administration may be presented as discrete patches adapted to remain in intimate contact with the epidermis of the recipient for a prolonged period of time. Such patches suitably contain the multivalent HIV inhibitor and optionally an additional antiviral agent: 1) in an optionally buffered, aqueous solution; or 2) dissolved and/or dispersed in an adhesive; or 3) dispersed in a polymer. A suitable concentration of each ingredient is about 1% to 25%, preferably about 5 to 15%.

Formulations of the present invention suitable for oral administration may be presented as discrete units such as capsules, caches or tablets, each containing a predetermined amount of the ingredients; as a powder or granules; as a solution or a suspension in an aqueous or non-aqueous liquid; or as an oil-in-water liquid emulsion or a water-in-oil liquid emulsion.

Formulations suitable for topical administration in the mouth include lozenges comprising one or more of the multivalent HIV inhibitors in a flavored basis, usually sucrose or acacia; pastilles comprising one or more of the ingredients in an inert basis such as gelatin and glycerin, or sucrose and acacia; and mouthwashes comprising the one or more of the ingredients in a suitable liquid carrier.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing, in addition to the one or more of the compounds of the present invention, such carriers as are known in the art to be appropriate.

For a perinatal subject, the drug combination of the present invention may be, for example, administered orally after 36 weeks of pregnancy and continued through delivery. Interventions around the time of late gestation and delivery (when the majority of transmissions are thought to occur) are most efficacious.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Methods and Materials

All Fmoc-protected amino acids used for peptide synthesis were purchased from Novabiochem. HATU, DIPEA and Fmoc-PAL-PEG-PS were purchased form Applied Biosystems. HPLC grade acetonitrile was purchased from Fisher Scientific. DMF was purchased from B & J Biosynthesis. 1,11-bisMaleimidotetraethyleneglycol (bi-maleimide-SS) was purchased from Pierce. All other chemicals were purchased from Pierce or Aldrich/Sigma and used as received. $^{1}H$ and $^{13}C$ NMR spectra were recorded on Inova 500 NMR machine. The ESI-MS spectra were measured on a Waters ZMD mass spectrometer. TLC was performed on glass plates coated with silica gel 60 F254 (E. Merck). Flash column chromatography was performed on silica gel 60 (EM Science, 230-400 mesh). Analytical HPLC was carried out with a Waters 626 HPLC instrument on a Waters Nova-Pak C18 column (3.9×150 mm) at 40° C. The column was eluted with a linear gradient of 0-70% MeCN containing 0.1% TFA at a flow rate of 1 mL/min over 20 minutes. Compounds were detected at 214 nm. Preparative HPLC was performed with a Waters 600 HPLC instrument of a Waters C18 column (Symmetry 300, 19×300 mm). The column was eluted with a suitable gradient of MeCN containing 0.1% TFA at 12 mL/min.

1,8-bis-(6-maleimidocaproylamido)-triethyleneglycol (bi-Maleimide-MS). To a solution of 2,2'-(Ethylenedioxy) bis-(ethylamine) (10 mg, 67 μmol) in THF (2 mL) containing a few drops of $NaHCO_3$ (0.1 M) was added N-(6-maleimidocaproyloxy)succinimide ester (EMCS) (42 mg, 135 μmol). After stirring for 3 h, the reaction mixture was condensed by a rotary evaporator under diminished pressure. The residue was subject to flash column chromatography using methanol/ethyl acetate (1:9, v/v) as the eluent to give bi-Maleimide-MS as a light white solid (29 mg, 81%): m.p. 112-114° C.; $^{1}H$ NMR (500 MHz, $CDCl_3$/TMS): δ 6.69 (s, 4H, 2 OH=CH), 5.99 (br. s, 2H, 2 NH), 3.62 (s, 4H, OCH$_2$CH$_2$O), 3.56 (t, 4H, J=5.2 Hz, 2 NCH$_2$CH$_2$O), 3.51 (t, 4H, J=7.2 Hz, 2 N—CH$_2$), 3.46 (q, 4H, J=5.3 Hz, 2 NCH$_2$CH$_2$O), 2.17 (t, 4H, J=7.4 Hz, 2 CH$_2$CON), 1.66 (q, 4H, J=7.5, 7.6 Hz, 2 CH$_2$C H$_2$CON), 1.60 (q, 4H, J=7.5, 7.4 Hz, 2 N—CH$_2$CH$_2$), 1.32 (q, 4H, J=7.5, 7.9 Hz, 2 N—CH$_2$CH$_2$ CH$_2$H$_2$CH$_2$CON); $^{13}$C NMR (500 MHz, CDCl$_3$/TMS) 134.05, 70.21, 69.92, 39.12, 37.62, 28.23, 26.32, 25.04; ESI-MS calcd. for C$_{26}$H$_{38}$N$_4$O$_8$ (M): 534.27; Found: 535.46 (M+H)$^+$.

1,8-bis-[6-(4-N-maleimidomethyl-cyclohexane-1-carboxyl)amido]caproxyl-triethyleneglycol (bi-Maleimide-LS)

A mixture of 2, 2'-(Ethylenedioxy)bis-(ethylamine) (4.1 mg, 28 µmol) and succinimidyl-4-(N-maleimidomethyl)-cyclohexane-1-carboxy-(6-amidocaproate) (LC-SMCC) (25 mg, 56 µmol) in THF (2 mL) containing NaHCO$_3$ was reacted as described for the preparation of bi-maleimide-SS. Column chromatography of the residue gave bi-Maleimide-LS as a light white solid (9 mg, 76%): m. p. 178-180° C.; $^1$H NMR (500 MHz, CDCl$_3$/TMS), δ 6.69 (s, 4H, 2 CH=CH), 6.22 (br. s, 2H, 2 NH), 5.78 (br. s, 2H, 2 NH), 3.62 (s, 4H, OCH$_2$CH$_2$O), 3.57 (t, 4H, J=5.3 Hz, 2 NCH$_2$CH$_2$O), 3.44 (m, 4H, 2 NCH$_2$CH$_2$O), 3.36 (d, 4H, 6.8 Hz, 2 N—CH$_2$), 3.21 (m, 4H, 2 CONHCH$_2$), 2.18 (t, 4H, J=7.4 Hz, 2 CH$_2$CONHCH$_2$CH$_2$O), 1.87 (m, 4H, 2 CH$_2$CONHCH$_2$CH$_2$O), 1.73 (m, 4H, 2 CH$_2$CONHCH$_2$CH$_2$), 1.62 (s, 8H, cyclohexane), 1.49 (t, 4H, J=6.8 Hz, CHCONHCH$_2$CH$_2$CH$_2$CH$_2$CH$_2$CONH), 1.44 (m, 2H, 2 cyclohexane—CHCH$_2$N), 1.42 (m, 2H, 2 cyclohexane-CHCONH), 1.33 (m, 4H, cyclohexane), 0.99 (m, 4H, cyclohexane); $^{13}$C NMR (500 MHz, CDCl$_3$/TMS) 133.96, 70.22, 69.88, 45.91, 43.64, 39.55, 38.98, 36.32, 36.30, 29.82, 29.20, 28.90, 26.31, 24.96; ESI-MS calcd. for C$_{42}$H$_{64}$N$_6$O$_{10}$ (M): 812.47; Found: 813.65 (M+H)$^+$ Peptide synthesis. Peptides were synthesized on a Pioneer automatic peptide synthesizer (Applied Biosystems) using fluorenylmethyloxycarbonyl (Fmoc)-protected amino acids as building blocks, 2-(1-H-azabenzotriazol-1-yl)-1,1,3,3-tetramethyluronium hexafluorophosphate (HATU) as the coupling reagent, and polyethylene glycol-polystyrene resin with a peptide amide linker (PAL-PEG-PS resin) as the solid support. Reduced peptide red-CD4M9-Cys was synthesized on a 0.2 mmole scale and cleaved from resin and deprotected as described previously (26). The crude peptide was precipitated in ethyl ether and purified through PR-HPLC to give red-CD4M9-Cys (320 mg, 52%). $t_R$=13.20 min (Under the analytical HPLC condition described in the general method); ESI-MS calcd. M=3089.83; Found: 1030.88 (M+3H)$^{3+}$, 773.43 (M+4H)$^{4+}$, and 619.12 (M+5H)$^{5+}$.

Folding of red-CD4M9-Cys. The reduced peptide red-CD4M9-Cys (37 mg, 12 µmol) was dissolved in degassed guanidine hydrochloride (1 M, 75 mL). Reduced glutathione (9.5 mg, 31 µmol) was added into the mixture followed by addition of oxidized glutathione (19 mg, 31 µmol). To the mixture was added a NaHCO$_3$ solution (0.1 M) to adjust pH to 8.5. The mixture was shaken under N$_2$ overnight when HPLC indicated the formation of a major single peak that moved faster then the reduced peptide. Lyophilization of the reaction mixture and subsequent HPLC purification gave the folding product CD4M9-Cys-Glutathione (30.5 mg, 75%). $t_R$=11.06 min (Under the analytical HPLC condition described in the general method); ESI-MS calcd. M=3389.08; Found: 1695.41 (M+2H)$^{2+}$, 1130.50 (M+3H)$^{3+}$, 848.29 (M+4H)$^{4+}$, 678.96 (M+5H)$^{5+}$, and 565.79 (M+6H)$^{6+}$.

Selective cleavage of the intermolecular disulfide bond to give CD4M9-Cys. The folded product CD4M9-Cys-Glutathione (15 mg, 4.4 µmol) was dissolved in degassed guanidine hydrochloride (30 mL, 1 M). To the solution was added tris[2-carboxyethyl]phosphine hydrochloride (TCEP) (7.57 mg, 26.4 µmol). The mixture was gently shaken for 10 hours and then lyophilized. HPLC purification gave the desired product CD4M9-Cys with a free cysteine at the C-terminus (10.6 mg, 78%). $t_R$=11.67 min (Under the analytical HPLC condition described in the general method); ESI-MS calcd. M=3083.16; Found: 1542.69 (M+2H)$^{2+}$, 1028.69 (M+3H)$^{3+}$, 771.91 (M+4H)$^{4+}$, and 617.75 (M+5H)$^{5+}$.

Tagging of the free cysteine in CD4M9-Cys with iodoacetamide. A solution of CD4M9-Cys (2 mg) in a phosphate buffer (1 mL, pH 8.0) was treated with iodoacetamide (50 mM) for 2 h at room temperature. RP-HPLC purification gave the acetamide-tagged miniprotein (2 mg, quantitative). $t_R$=11.62 min (Under the analytical HPLC condition described in the general method); ESI-MS calcd. M=3141.12; Found: 1047.98 (M+3H)$^{3+}$, 786.26 (M+4H)$^{4+}$, and 629.20 (M+5H)$^{5+}$.

Proteolytic digestion and Edman degradation. The above-described acetamide-tagged miniprotein (1.5 mg, 1 mg/mL) was treated with trypsin and chymotrypsin (20 µL, 0.5 mg/mL each) at room temperature in 50 mM Tris buffer (pH 8.3) containing 0.005% Triton X-100 and 20 mM CaCl$_2$. The reaction was monitored by analytical RP-HPLC (monitored at 214 nm) and the peptide fragments were isolated and subject to ESI-MS analysis. A major fragment with a mass of 1486.2 Da (fragment c) was subject to one-step manual Edman degradation. Briefly, the peptide was suspended in pyridine/water (1:1, 300 µL), to which 20 µL phenylisothiocyanate (PITC) was added. The mixture was incubated at 50° C. for 30 min and the solvent was removed under vacuum. TFA (200 µL) was added and the mixture was reacted at 50° C. for 15 min to cleave the N-terminal residues. TFA was removed under vacuum and the residue was suspended in water (200 µL). After extraction with pentane/ethyl acetate (4:1, 200 µL), the aqueous solution was subject to HPLC and the fragments were isolated and analyzed by ESI-MS. Again, a major fragment with a mass of 874.1 Da (fragment g) was isolated and was subject to two steps of Edman degradation following the procedures described above. The degradation products were analyzed by HPLC and ESI-MS.

General procedures for chemoselective ligation of CD4M9-Cys with bis-maleimide scaffold. CD4M9-Cys (1.2 mol. equiv. per maleimide functionality) was dissolved in degassed phosphate buffer (50 mM, pH 6.6) containing 50% acetonitrile. Then a solution of bis-maleimide scaffold (bi-maleimide-SS, bi-maleimide-MS, or bi-maleimide-LS) in acetonitrile was added. The mixture was gently shaken under N$_2$ at room temperature. The processing of ligation was monitored with analytic HPLC and the reaction was complete within 1-2 hours. The ligation product was purified and characterized by ESI-MS.

Bi-CD4M9-SS (with a shorter spacer): 90% yield; $t_R$ 12.20 min (Under the analytical HPLC condition described in the general method); ESI-MS calcd. M=6520.50; Found: 1305.08 (M+5H)$^{5+}$, 1087.74 (M+6H)$^{6+}$, 932.54 (M+7H)$^{7+}$, 816.12 (M+8H)$^{8+}$, 725.54 (M+9H)$^{9+}$.

Bi-CD4M9-MS (with a medium spacer): 80% yield; $t_R$ 12.37 min (Under the analytical HPLC condition described in the general method); ESI-MS calcd. M=6703.50; Found: 1118.18 (M+6H)$^{6+}$, 958.56 (M+7H)$^{7+}$, 838.97 (M+8H)$^{8+}$, 745.83 (M+9H)$^{9+}$, 671.37 (M+10H)$^{10+}$.

Bi-CD4M9-LS (with a longer spacer): 56% yield; $t_R$ 12.66 min (Under the analytical HPLC condition described in the general method); ESI-MS calcd. M=6980.97; Found: 1164.50 $(M+6H)^{6+}$, 998.34 $(M+7H)^{7+}$, 873.71 $(M+8H)^{8+}$, 776.77 $(M+9H)^{9+}$, 699.20 $(M+10H)^{10+}$, 635.76 $(M+11H)^{11+}$.

Anti-viral assays. Peripheral blood mononuclear cells (PBMCS) were separated from whole blood of HIV-seronegative donors by density centrifugation over Ficoll-Hypaque (Sigma). The culture medium consisted of RPMI supplemented with 10% fetal bovine serum (FBS), 2 mM glutamine and penicillin/streptomycin (Gibco, Grand Island, N.Y.). For infection studies, PBMCs were stimulated with 2.5 µg/ml phytohemagglutinin (PHA; Boehringer Mannheim, Indianapolis, Ind.) for 3 days. Stimulated PBMCs were infected by incubation with HIV-$1_{IIIB}$ at a multiplicity of infection of 1000 $TCID_{50}/10^6$ PBMC for 2 h. PBMCs were then washed three times with PBS and cultured at 37° C. in RPMI/10% FBS supplemented with 100 units/ml rIL-2 (Boehringer Mannheim) and the bivalent inhibitors at varied concentrations. PBMCs were seeded in 96-well flat-bottom plates at a density of $2\times10^5$ PBMCs/200 µl. Following 3 days of culture, half of the medium was replaced with fresh medium containing IL-2 and the antiviral agents. After 7 days of culture, virus production in the culture supernatant was assayed by measuring HIV-1 reverse transcriptase (RT) activity as described (27). Cell viability in culture in the presence or absence of antiviral agents was measured by commercial MTT assay, as per the manufacturer's instructions (Boehringer Mannheim).

Design of the Multivalent HIV Inhibitors. Although the crystal structure of the truncated gp120 core has been solved (4), the atomic structure of the proposed gp120 trimer is not known, and as such, it was assumed that the trimeric model of gp120 was constrained to be threefold symmetric. The distance across the three Phe43 cavities of the CD4-binding sites in the trimeric gp120 was determined and it was found that the trimeric complex of gp120 is a dynamic structure and the distance between any two of the Phe43 cavities was estimated to be in the range of 30-55 Å (FIG. 1A). To match the distance between any two of the CD4-binding cavities, bivalent miniproteins were designed by tethering two CD4M9 moieties through a linker of varied length. A general structure of the designed bivalent inhibitors is shown in FIG. 1B. For constructing such a covalently-linked bivalent miniprotein, we decided to introduce an extra cysteine residue at the C-terminus of CD4M9 as a tag for late-stage chemoselective ligation, because the model of the interaction between CD4M9 and gp120 suggested that the C-terminus of CD4M9 did not have any contact with residues of gp120 and was pointed away from the binding sites (12). The length and flexibility of the linker are critical to place the two CD4M9 moieties in an appropriate spatial position to match the two binding sites in the trimeric gp120, and as such, the optimal length was determined by probing with different lengths of the linker.

Figure 4:
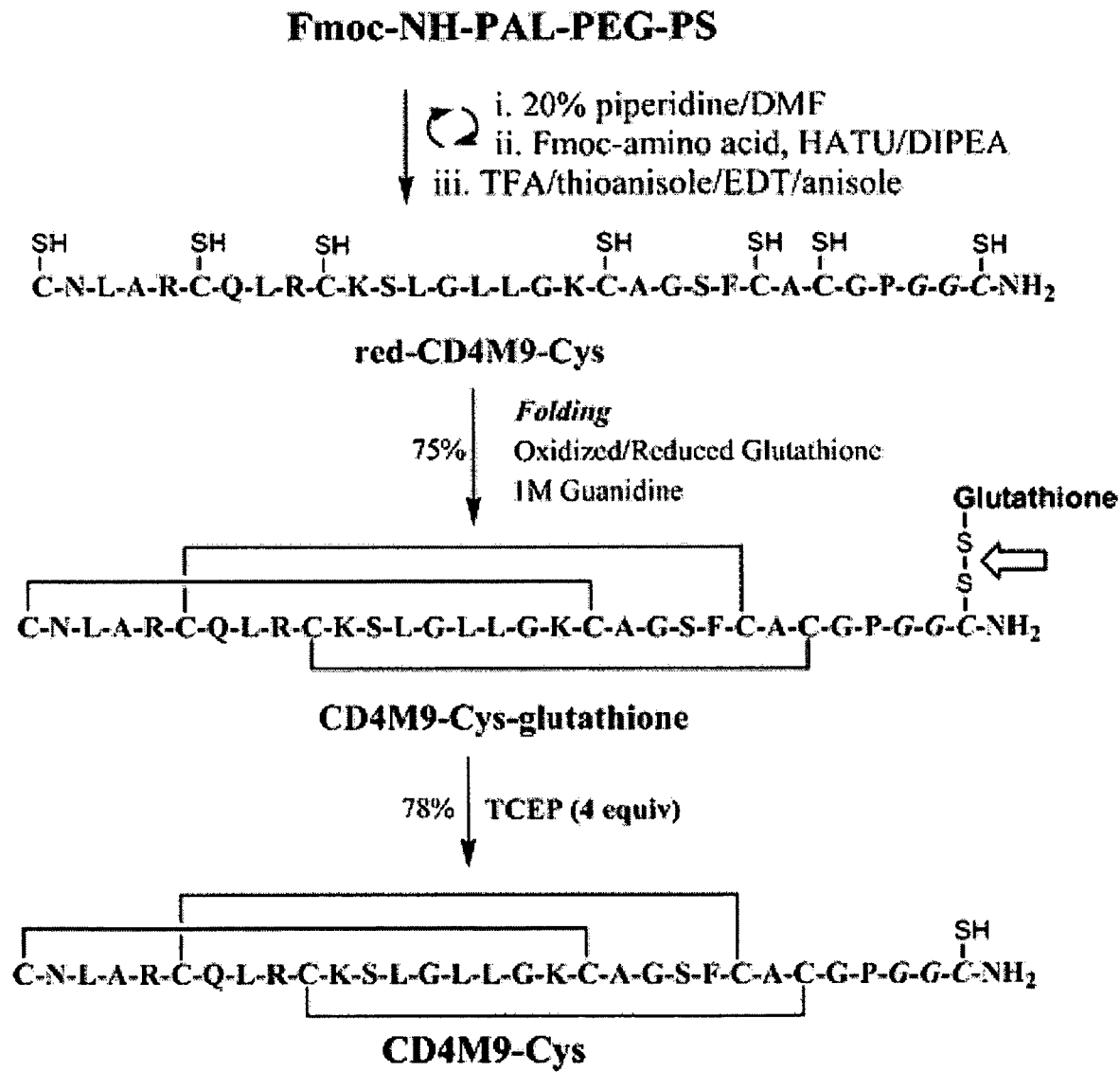
FIG. 4 shows the synthesis of cysteine-tagged miniprotein CD4M9-Cys (SEQ ID NO: 3) beginning with the corresponding reduced CD4M9-Cys (SEQ ID NO: 3) involving the intermediate CD4M9-Cys-glutathione (SEQ ID NO: 4).

Synthesis of a modified miniprotein CD4M9-Cys. For chemoselective conjugation, a tripeptide sequence GGC was added to the C-terminus of the CD4M9 sequence to give a 31-amino acid peptide. The reduced, 31-mer precursor was synthesized by solid-phase peptide synthesis using Fmoc-chemistry. After HPLC purification, the reduced peptide was then folded in the presence of reduced/oxidized glutathione in a 1M guanidine-HCl solution. HPLC monitoring indicated that the folding proceeded smoothly to give a major product. The expected mass of the folded miniprotein would be 3083.16 Da, whereas ESI-MS analysis of the folding product gave a molecular mass of 3389.1 Da, indicating the introduction of a glutathione moiety to the folded molecule. The glutathione moiety was most likely linked to the molecule through an intermolecular disulfide bond formation with the extra cysteine residue in the molecule. This notion was confirmed by the selective cleavage of the intermolecular disulfide linkage. Thus, treatment of the glutathione-tagged protein with tris[2-carboxyethyl]phosphine hydrochloride (TCEP) selectively removed the glutathione moiety to give the miniprotein CD4M9-Cys as shown in FIG. 4. It should be pointed out that using other reducing agents such as DTT and β-mercaptoethanol resulted in a complicated mixture (as revealed by HPLC monitoring), probably due to simultaneous cleavage of intramolecular disulfide bonds and subsequent mis-folding of the protein (thiol-disulfide shuffling). The product CD4M9-Cys was purified by HPLC and analyzed by ESI-MS spectrometry. As described in the experimental section, the molecular mass of the reduced miniprotein red-CD4M9-Cys was found to be 3089.6 Da, while the molecular mass of the final, folded miniprotein CD4M9-Cys was found to be 3083.38 Da. A 6-Dalton difference in molecular mass of the reduced and folded forms clearly indicated the formation of three pairs of disulfide bonds in the folded miniprotein CD4M9-Cys with an extra free cysteine residue.

Figure 7:
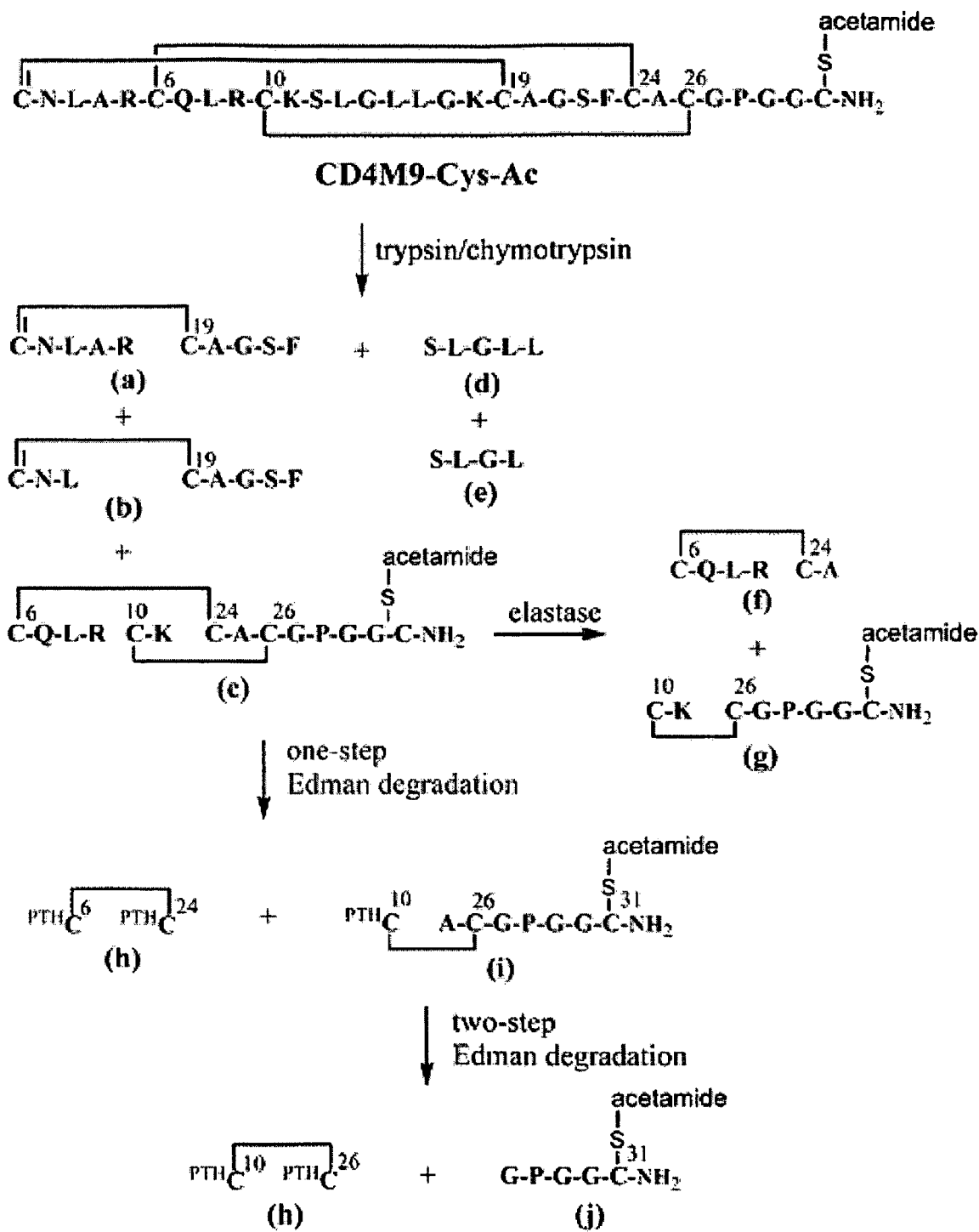
FIG. 7 shows the validation of the miniprotein's folding pattern by proteolytic digestion and Edman Degradation, using an acetamide-tagged cysteine, CD4M9-Cys-Ac (SEQ ID NO: 5), which was subjected to digestion/degradation to produce the following fragment moieties: CNLAR (SEQ ID NO: 6); CAGSF (SEQ ID NO: 7); CNL (SEQ ID NO: 8); CQLR (SEQ ID NO: 9); CK (SEQ ID NO: 10); CACGPGGX where X=cysteine-S-acetamide (SEQ ID NO: 11); SLGLL (SEQ ID NO: 12); SLGL (SEQ ID NO: 13); CA (SEQ ID NO: 14); CGPGGX where X=cysteine-S-acetamide (SEQ ID NO: 15); CC (SEQ ID NO: 16); ACGPGGX where X cysteine-S-acetamide (SEQ ID NO: 17); and GPGGX where X=cysteine-S-acetamide (SEQ ID NO: 18).

Validation of correct folding of the modified miniprotein. CD4M9-Cys was modified from the known miniprotein CD4M9 by introducing a three peptide sequence GGC at the C-terminus. The disulfide connectivity of CD4M9 was previously assigned as $C^1$-$C^{19}$, $C^6$-$C^{24}$, and $C^{10}$-$C^{26}$ (12). The NMR structure of CD4M9 and the molecular modeling of the complex of CD4M9 with gp120 indicated that the C-terminus was pointing away from the folding core and did not seem to be involved in direct interaction with gp120 (12, 13). Therefore, it was assumed that introduction of a sequence GGC at the C-terminus would not interrupt the folding of the protein. However, it was still possible that the introduction of an extra cysteine in the molecule may lead to mis-folding through a thiol-disulfide shuffling. As such to validate the disulfide connectivity in the folded CD4M9-Cys, proteolytic digestion of the miniprotein was preformed and subsequent Edman degradation of key peptide fragments, following a recently published procedure (28). As shown in FIG. 7, the free cysteine in CD4M9-Cys was tagged with an acetamide group for final identification. The tagged protein was then digested with trypsin and chymotrypsin. Trypsin is specific for amides with positively charged side-chains, e.g., Lys and Arg, while chymotrypsin is specific for amides with aromatic or other large hydrophobic side-chains such as Phe and Leu. Treatment of the acetamide-tagged CD4M9-Cys with trypsin and chymotrypsin yielded several major fragments that were separated by reverse phase HPLC. ESI-MS analysis of the peptide fragments gave the information on their molecular masses: 1057.5 Da, 829.4 Da, 1486.2 Da, 501.4 Da, and 388.3 Da, corresponding to the Fragments a-e, respectively as shown in Table 1 and FIG. 7.

TABLE 1

| Fragments (#) | MW (Da) Calcd | MW (Da) Found | HPLC ($t_R$, min) |
| --- | --- | --- | --- |
| (a) | 1057.5 | 1057.5 | 7.95[(1)] |
| (b) | 829.9 | 829.4 | 8.56[(1)] |
| (c) | 1486.3 | 1486.2 | 6.12[(1)] |
| (d) | 501.6 | 501.4 | 10.11[(1)] |
| (e) | 388.2 | 388.3 | 8.80[(1)] |
| (f) | 708.4 | 708.5 | 7.93[(1)] |
| (g) | 795.2 | 795.7 | 8.05[(1)] |
| (h) | 510.3 | 510.9 | 9.62[(2)] |
| (i) | 874.8 | 874.1 | 11.27[(2)] |
| (j) | 447.1 | 447.4 | 12.34[(2)] |

The isolation of Fragments (a) and (b) clearly indicated a disulfide pairing between $C^1$ and $C^{19}$. To determine the next disulfide connectivity, Fragment (c) was subject to enzymatic hydrolysis with elastase, which is specific for Ala residue. Elastase treatment resulted in formation of Fragment (f) (708.5 Da) and Fragment (g) (795.7 Da). The formation of Fragment (f) indicated that $C^6$ was paired with $C^{24}$ in the folded protein, because the connection of $C^6$ with any other cysteine residues would not give Fragment (f) after elastase treatment. This was further verified by one-step Edman degradation of Fragment (c). Edman degradation would tag all the three N-terminal amino acid residues with a phenylthiohydantoin (PTH) derivative and simultaneously cleave the first amide bonds from the three N-termini. The identification of Fragment (h) (510.9 Da) and Fragment (i) (874.1 Da) confirmed the assignment of $C^6$-$C^{24}$ connection. Finally, to determine whether $C^{10}$ was connected to C26 or $C^{31}$, the Fragment (i) was subject to two-step Edman degradation to give two fragments, Fragment (h) and Fragment (j) (447.4 Da). The identification of these two fragments unambiguously confirmed the disulfide connection between $C^{10}$ and $C^{26}$. It should be pointed out that the Fragment (j) somehow appeared very hydrophobic compared to other fragments under the reverse-phase HPLC conditions (Table 1). Taken together, the enzymatic digestion coupled with Edman degradation unambiguously verified the assumed folding pattern of CD4M9-Cys, which would have a free cysteine at the C-terminus and bear the following disulfide connectivity: $C^1$-$C^{19}$, $C^6$-$C^{24}$, and $C^{10}$-$C^{26}$.

To confirm that the synthetic miniprotein maintains the same activity as the parent compound CD4M9, anti-HIV assays of the synthetic CD4M9-Cys were performed and the results were compared with activity of a standard CD4M9. Both miniproteins showed no difference in anti-HIV activities in our assays with peripheral blood mononuclear cells (PBMCs) as the host cells with infection by HIV-1$_{IIIB}$. The IC50 (concentration for 50% inhibition of HIV infection) for both CD4M9-Cys and CD4M9 was found to be 1-5 μM, depending on the donors of PBMCs. The results further suggested that the protein was properly folded and the introduction of a C-terminal tag GGC did not seem to interfere with its anti-HIV activity.

Figure 2:
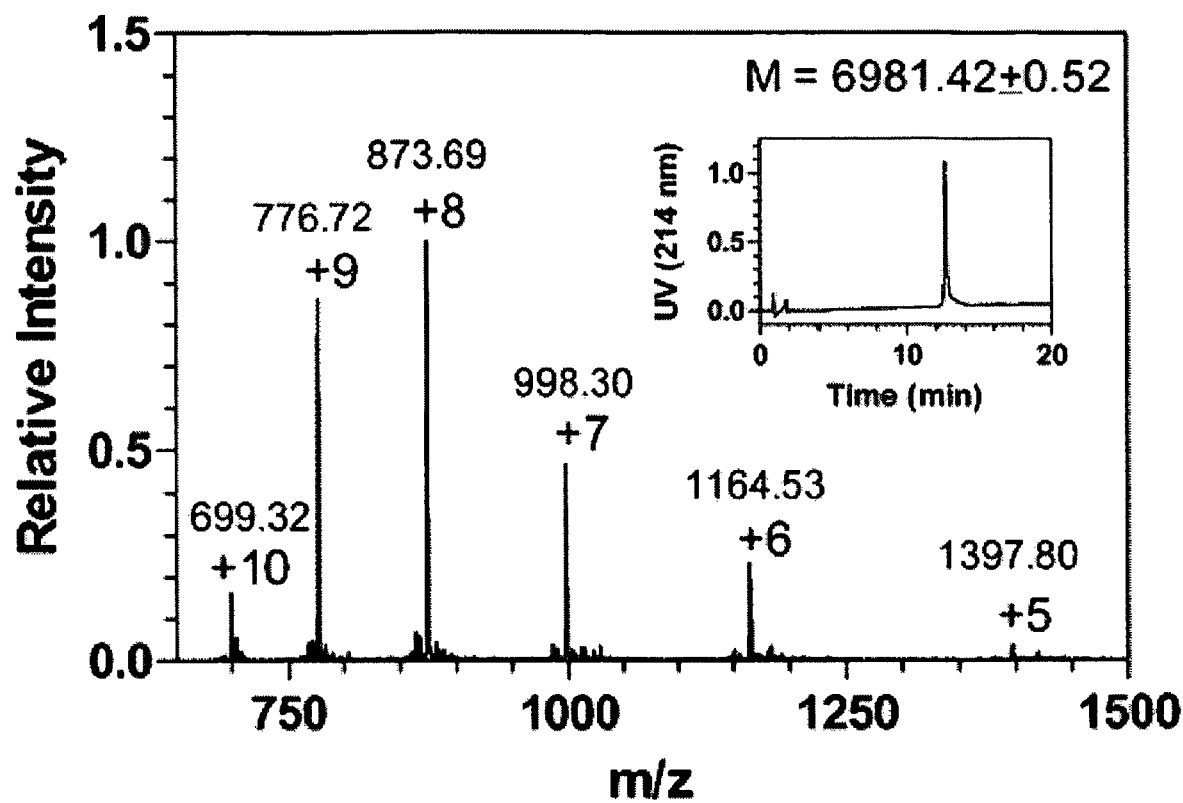
FIG. 2 shows the ESI-MS and HPLC profiles of the bivalent miniprotein bi-CD4M9-LS. Analytical HPLC was performed on a Waters Nova-Pak C18 column (3.9×150 m) at 40° C. The column was eluted with a linear gradient of 0-70% MeCN containing 0.1% TFA at a flow rate of 1 mL/min over 20 min (detection: 214 nm).
Figure 5:
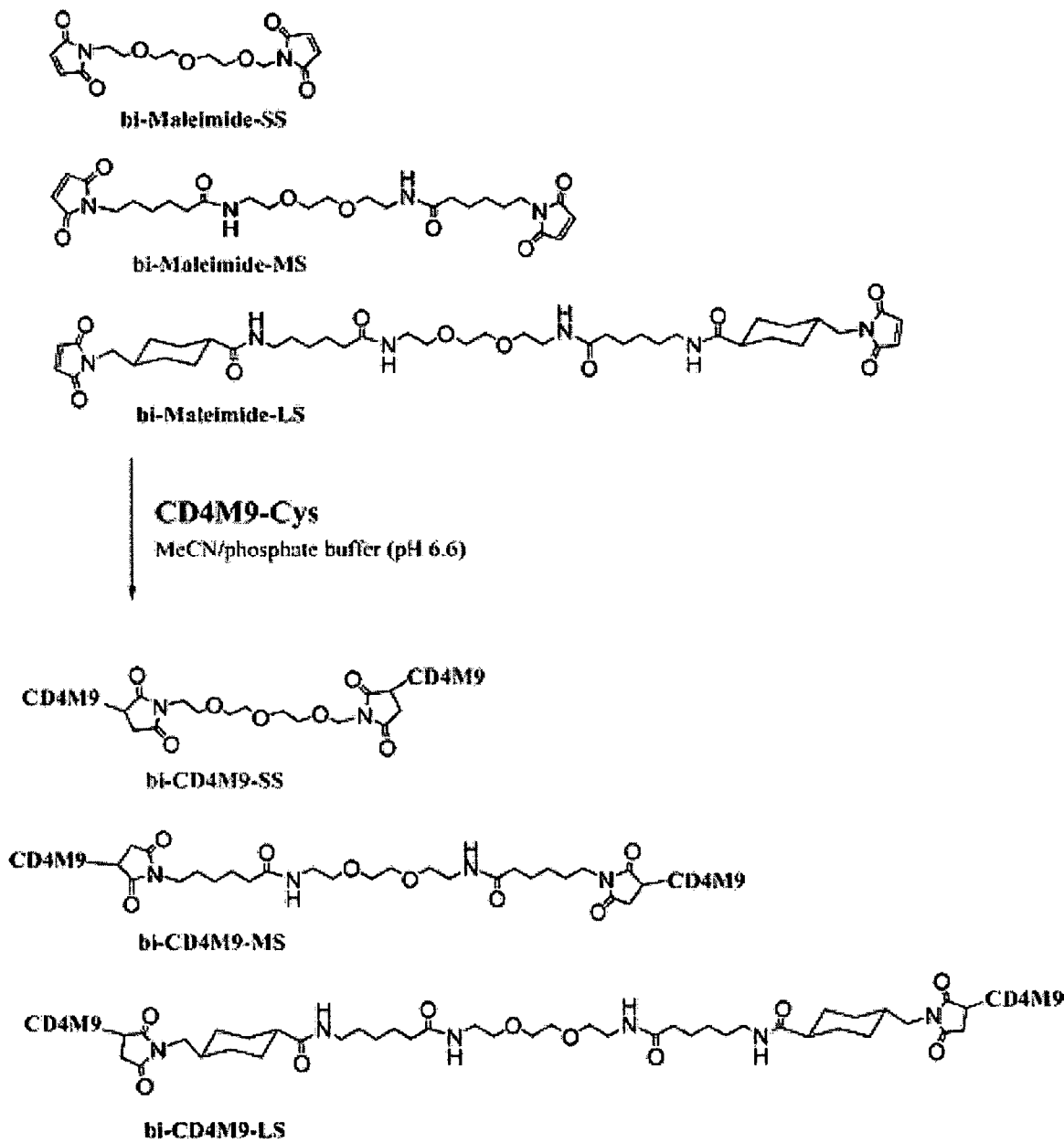
FIG. 5 shows the synthesis of bivalent CD4M9 inhibitors with different lengths of a spacer/linker.

Synthesis of bivalent miniproteins. To construct the bivalent CD4M9 inhibitors, three bivalent maleimides were chosen as the scaffolds, in which the maleimide moieties were spaced at a maximum of 18 Å, 32 Å and 44 Å in distance, respectively. The ligation of the scaffold and CD4M9-Cys was performed in a phosphate buffer (pH 7.2) containing acetonitrile to give the corresponding bivalent miniproteins bi-CD4M9-SS, bi-CD4M9-MS, and bi-CD4M9-LS with a short, medium, and a long spacer, respectively as shown in FIG. 5. The products were purified by HPLC and characterized by ESI-MS. A typical HPLC and ESI-MS profiles for the purified bivalent minprotein bi-CD4M9-LS was shown in FIG. 2, which indicates the purity and identity of the ligation product. Based on the folded structure of CD4M9 (12), the distance between the C-terminal Cys in CD4M9-Cys and the Phe residue, which binds to the "Phe43 cavity" of gp120, was estimated to be ca. 10 Å. Therefore, it was deduced that the maximal distance between the two Phe groups in the synthetic bivalent miniproteins would be 38 Å, 52 Å, and 64 Å for bi-CD4M9-SS, bi-CD4M9-MS, and bi-CD4M9-LS, respectively. The maximal distance of the two Phe-ligands in the synthetic bivalent ligands falls into the estimate range of 30-60 Å between any two of the three "Phe43 cavities" in the modeled trimeric gp120 complex (17).

Figure 3:
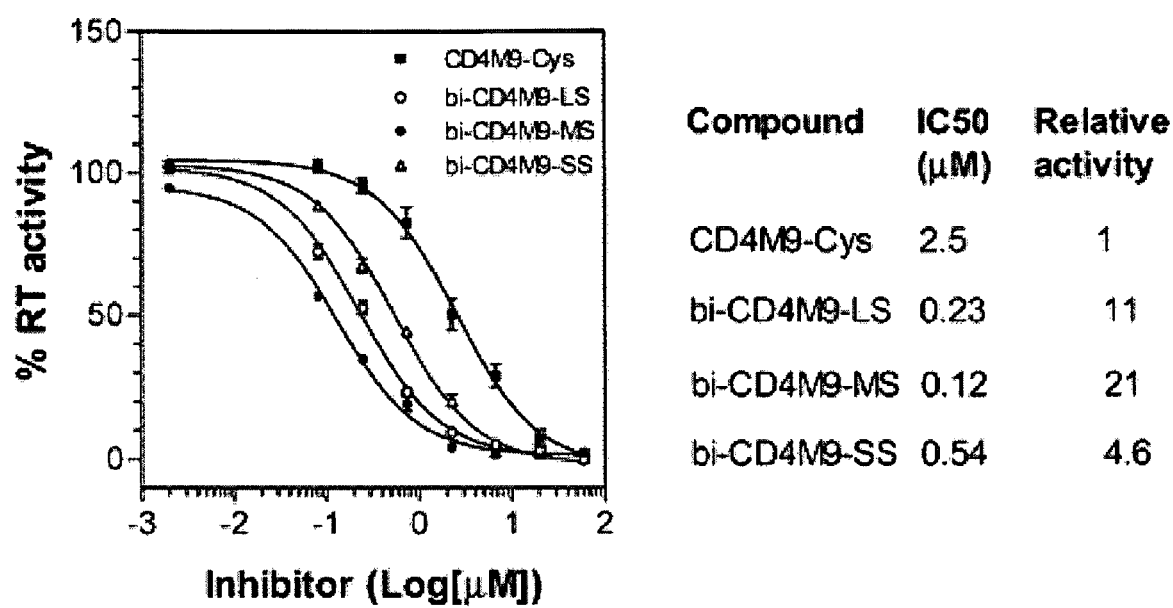
FIG. 3 shows inhibition of HIV-1 infection by bivalent CD4M9. PBMCs were infected by HIV-$1_{IIIB}$ in the presence or absence of the synthetic miniproteins at various concentrations. Virus production was assessed by measuring viral reverse transcriptase (RT) activity. The IC50 was defined as the concentration that reaches 50% inhibition of viral production.

Evaluation of anti-HIV activity of the synthetic bivalent miniproteins. The antiviral activity of the synthetic bivalent inhibitors was examined on donor peripheral blood mononuclear cells (PBMCs) infected with HIV-1$_{IIIB}$. All the bivalent miniproteins showed enhanced anti-HIV activity over the monovalent miniprotein CD4M9-Cys as shown in FIG. 3. In comparison, the best bivalent miniprotein bi-CD4M9-MS, in which the two Phe residues could be spaced in a maximal distance of 52 Å, showed a 21-fold increase of anti-HIV activity over the monovalent inhibitor. The bivalent inhibitors bi-CD4M9-SS (with a shorter spacer) and bi-CD4M9-LS (with a longer spacer) showed a 4.6 and 11-fold increase over the monovalent inhibitor, respectively. Although direct binding studies of the synthetic bivalent inhibitors with reconstituted oligomeric gp120 (14, 15) have not been preformed, it is assumed that this activity enhancement could be resulted directly from the enhanced binding of the bivalent inhibitors to the multivalent CD4-binding sites of the trimeric gp120 complex. The difference in activities among the bivalent inhibitors with a linker of varied length suggests that the two binding ligands in the bivalent miniproteins should be spaced adequately to match the binding sites on the trimeric gp120, so that a simultaneous multivalent interaction can occur to achieve a high affinity binding.

Figure 6:
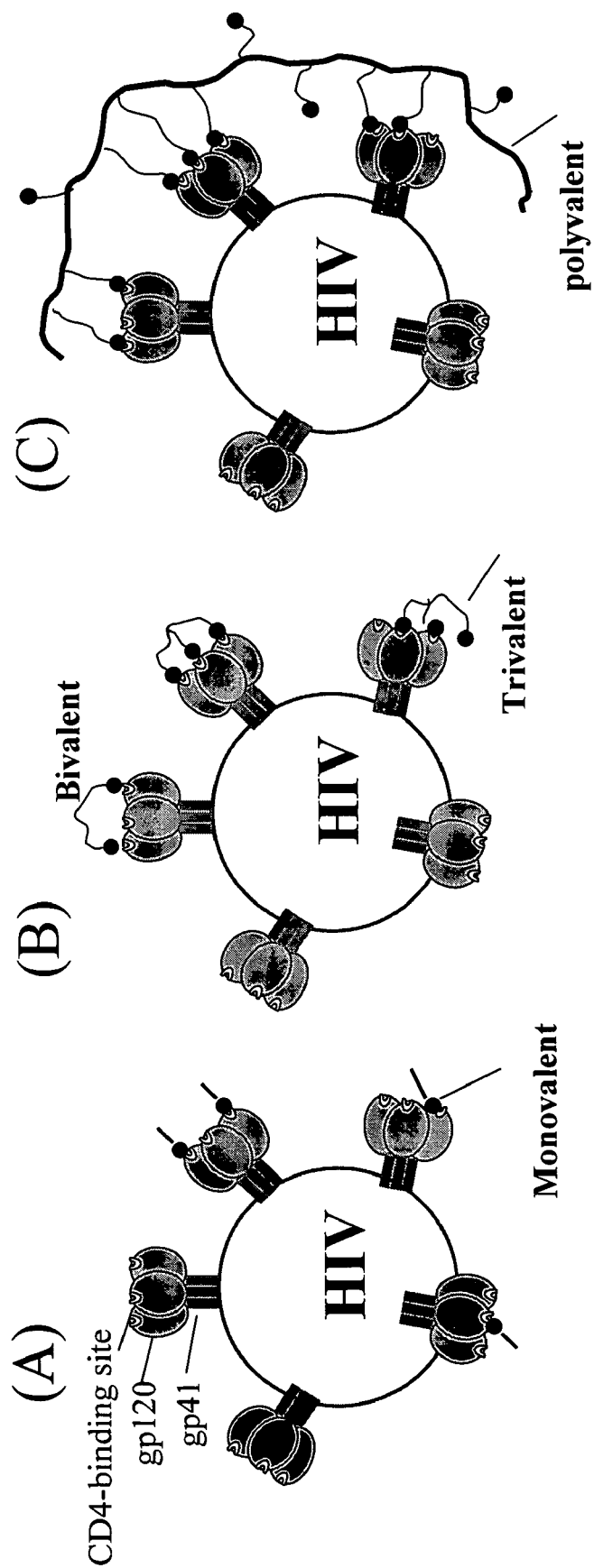
FIGS. 6 A, B and C illustrate binding of mono (A), bi-, tri-(B), and poly-valent (C) inhibitors to gp120.

In conclusion, the results demonstrated that creation of simple bivalent inhibitors leads to a significant enhancement of anti-HIV activity over the corresponding monovalent inhibitor. Further, the results indicate that attacking the multivalent target, the oligomeric gp120, by creating a multivalent ligand constitutes a valuable approach toward effective HIV inhibition. As such, as shown in FIG. 6, a trivalent or multivalent ligand that occupies three CD4-binding sites in the trimeric gp120 complex simultaneously clearly further inhibits HIV infection.

LITERATURE CITED

References cited herein are hereby incorporated by reference herein for all purposes.

(1) Richman, D. D. (2001) HIV chemotherapy. *Nature* 410, 995-1001.
(2) Wensing, A. M., and Boucher, C. A. (2003) Worldwide transmission of drug-resistant HIV. *AIDS Rev.* 5, 140-155.
(3) Chan, D. C., and Kim, P. S. (1998) HIV entry and its inhibition. *Cell* 93, 681-684.
(4) Kwong, P. D., Wyatt, R., Robinson, J., Sweet, R. W., Sodroski, J., and Hendrickson, W. A. (1998) Structure of an HIV gp120 envelope glycoprotein in complex with the CD4 receptor and a neutralizing human antibody. *Nature* 393, 648-659.
(5) Wyatt, R., Kwong, P. D., Desjardins, E., Sweet, R. W., Robinson, J., Hendrickson, W. A., and Sodroski, J. G. (1998) The antigenic structure of the HIV gp120 envelope glycoprotein. *Nature* 393, 705-711.
(6) Smith, D. H., Byrn, R. A., Marsters, S. A., Gregory, T., Groopman, J. E., and Capon, D. J. (1987) Blocking of HIV-1 infectivity by a soluble, secreted form of the CD4 antigen. *Science* 238, 1704-1707.
(7) Traunecker, A., Luke, W., and Karjalainen, K. (1988) Soluble CD4 molecules neutralize human immunodeficiency virus type 1. *Nature* 331, 84-86.
(8) Deen, K. C., McDougal, J. S., Inacker, R., Folena-Wasserman, G., Arthos, J., Rosenberg, J., Maddon, P. J., Axel, R., and Sweet, R. W. (1988) A soluble form of CD4 (T4) protein inhibits AIDS virus infection. *Nature* 331, 82-84.
(9) Burton, D. R., Pyati, J., Koduri, R., Sharp, S. J., Thornton, G. B., Parren, P. W., Sawyer, L. S., Hendry, R. M., Dunlop, N., Nara, P. L., Lamacchia, M., Garratty, E., Stiehm, E. R., Bryson, Y. T., Moore, J. P., Ho, D. D., and Barbas, C. F. (1994) Efficient neutralization of primary isolates of HIV-1 by a recombinant human monoclonal antibody. *Science* 266, 1024-1027.

(10) Saphire, E. O., Parren, P. W., Pantophlet, R., Zwick, M. B., Morris, G. M., Rudd, P. M., Dwek, R. A., Stanfield, R. L., Burton, D. R., and Wilson, I. A. (2001) Crystal structure of a neutralizing human IGG against HIV-1: a template for vaccine design. *Science* 293, 1155-1159.

(11) Martin, L., Barthe, P., Combes, O., Roumestand, C., and Vita, C. (2000) Engineering novel bioactive mini-proteins on natural scaffolds. *Tetrahedron* 56, 9451-9460.

(12) Vita, C., Drakopoulou, E., Vizzavona, J., Rochette, S., Martin, L., Menez, A., Roumestand, C., Yang, Y. S., Ylisastigui, L., Benjouad, A., and Gluckman, J. C. (1999) Rational engineering of a miniprotein that reproduces the core of the CD4 site interacting with HIV-1 envelope glycoprotein. *Proc. Natl. Acad. Sci. USA* 96, 13091-13096.

(13) Martin, L., Stricher, F., Misse, D., Sironi, F., Pugniere, M., Barthe, P., Prado-Gotor, R., Freulon, I., Magne, X., Roumestand, C., Menez, A., Lusso, P., Veas, F., and Vita, C. (2003) Rational design of a CD4 mimic that inhibits HIV-1 entry and exposes cryptic neutralization epitopes. *Nat. Biotechnol.* 21, 71-76.

(14) Sanders, R. W., Vesanen, M., Schuelke, N., Master, A., Schiffner, L., Kalyanaraman, R., Paluch, M., Berkhout, B., Maddon, P. J., Olson, W. C., Lu, M., and Moore, J. P. (2002) Stabilization of the soluble, cleaved, trimeric form of the envelope glycoprotein complex of human immunodeficiency virus type 1. *J. Virol.* 76, 8875-8889.

(15) Schulke, N., Vesanen, M. S., Sanders, R. W., Zhu, P., Lu, M., Anselma, D. J., Villa, A. R., Parren, P. W., Binley, J. M., Roux, K. H., Maddon, P. J., Moore, J. P., and Olson, W. C. (2002) Oligomeric and conformational properties of a proteolytically mature, disulfide-stabilized human immunodeficiency virus type 1 gp140 envelope glycoprotein. *J. Virol.* 76, 7760-7776.

(16) Salzwedel, K., and Berger, E. A. (2000) Cooperative subunit interactions within the oligomeric envelope glycoprotein of HIV-1: functional complementation of specific defects in gp120 and gp41. *Proc. Natl. Acad. Sci. USA* 97, 12794-12799.

(17) Kwong, P. D., Wyatt, R., Sattentau, Q. J., Sodroski, J., and Hendrickson, W. A. (2000) Oligomeric modeling and electrostatic analysis of the gp120 envelope glycoprotein of human immunodeficiency virus. *J. Virol.* 74, 1961-1972.

(18) Staropoli, I., Chanel, C., Girard, M., and Altmeyer, R. (2000) Processing, stability, and receptor binding properties of oligomeric envelope glycoprotein from a primary HIV-1 isolate. *J. Biol. Chem.* 275, 35137-35145.

(19) Zhu, P., Chertova, E., Bess, J., Jr., Lifson, J. D., Arthur, L. O., Liu, J., Taylor, K. A., and Roux, K. H. (2003) Electron tomography analysis of envelope glycoprotein trimers on HIV and simian immunodeficiency virus virions. *Proc. Natl. Acad. Sci. USA* 100, 15812-15817.

(20) Mammen, M., Choi, S. K., and Whitesides, G. M. (1998) Polyvalent interactions in biological systems: Implications for design and use of multivalent ligands and inhibitors. *Angew. Chem. Int. Ed.* 37, 2754-2794.

(21) Kitov, P. I., Shimizu, H., Homans, S. W., and Bundle, D. R. (2003) Optimization of tether length in nonglycosidically linked bivalent ligands that target sites 2 and 1 of a Shiga-like toxin. *J. Am. Chem. Soc.* 125, 3284-3294.

(22) Dekker, F. J., de Mol, N. J., van Ameijde, J., Fischer, M. J., Ruijtenbeek, R., Redegeld, F. A., and Liskamp, R. M. (2002) Replacement of the intervening amino acid sequence of a Syk-binding diphosphopeptide by a nonpeptide spacer with preservation of high affinity. *Chembiochem* 3, 238-242.

(23) Kitov, P. I., Sadowska, J. M., Mulvey, G., Armstrong, G. D., Ling, H., Pannu, N. S., Read, R. J., and Bundle, D. R. (2000) Shiga-like toxins are neutralized by tailored multivalent carbohydrate ligands. *Nature* 403, 669-672.

(24) Fan, E., Zhang, Z., Minke, W. E., Hou, Z., Verlinde, C. L. M. J., and Hol, W. G. J. (2000) High-affinity pentavalent ligands of *E. coli* heat-labile enterotoxin by modular structure-based design. *J. Am. Chem. Soc.* 122, 2663-2664.

(25) Kiessling, L. L., Gestwicki, J. E., and Strong, L. E. (2000) Synthetic multivalent ligands in the exploration of cell-surface interactions. *Curr. Opin. Chem. Biol.* 4, 696-703.

(26) Wang, L. X., Ni, J., and Singh, S. (2003) Carbohydrate-centered maleimide cluster as new types of templates for multivalent peptide assembling: Synthesis of multivalent HIV-1 gp41 peptides. *Bioorg. Med. Chem.* 11, 129-136.

(27) Willey, R. L., Smith, D. H., Lasky, L. A., Theodore, T. S., Earl, P. L., Moss, B., Capon, D. J., and Martin, M. A. (1988) In vitro mutagenesis identifies a region within the envelope gene of the human immunodeficiency virus that is critical for infectivity. *J. Virol.* 62, 139-147.

(28) Wu, Z., Prahl, A., Powell, R., Ericksen, B., Lubkowski, J., and Lu, W. (2003) From pro defensins to defensins: synthesis and characterization of human neutrophil pro alpha-defensin-1 and its mature domain. *J. Pept. Res.* 62, 53-62

That which is claimed is:

1. A bivalent complex comprising:
    two gp120 binding molecules that target the CD4 binding pocket on a trimeric HIV gp120 complex; and
    a flexible bivalent spacer/linker attached to the gp120 binding molecules and positioned therebetween, wherein the flexible bivalent spacer/linker is of sufficient length to provide for binding of the gp120 binding molecules to the CD4 binding sites on the trimeric HIV gp120 complex.

2. The bivalent complex according to claim 1, wherein the distance between the gp120 binding molecules when attached to the flexible bivalent spacer/linker is in the range between 30 to 60 Å.

3. The bivalent complex according to claim 1, wherein the distance between the gp120 binding molecules when attached to the flexible bivalent spacer/linker is in the range between 50 to 55 Å.

4. The bivalent complex according to claim 1, wherein the gp120 binding molecule is a molecule that targets and binds to a "Phe43 cavity" on the trimeric HIV gp120 complex.

5. The bivalent complex according to claim 1, wherein the gp120 binding molecule is CD4M9, CD4M33, BMS378806 or BMS488043.

6. The bivalent complex according to claim 1, wherein the flexible bivalent spacer/linker comprises tris(2-carboxyethyl) phosphine hydrochloride; tris-succinimidyl aminotriacetate; tris-(2-maleimidoethyl)amine; 5, 5'-Dithio-bis-(2-nitobenzoic acid); bis-[β-(4-zaidosalicylamido)ethyl]disulfide; 1,4-bis-maleimidobutane; 1,4-bis-maleimidyl-2,3-dihydroxybutane; bis-maleimidohexane; bis-maleimidoethane; 1,8-bis-maleimidotriethyleneglycol; 1,8-bis-(6-maleimidocaproylamido)-triethyleneglycol; 1,8-bis-[6-(4-N-maleimidomethyl-cyclohexane-1-carboxyl)amido]caproxyl-triethyleneglycol; 1,11-bis-maleimidotetraethyleneglycol; bis[2-(Succinimidyloxycarbonyloxy)-ethyl]sulfone; bis[Sulfosuccinimidyl]suberate; disuccinimidyl glutarate; dithiobis(succinimidyl propionate); disuccinimidyl suberate; dithia-bis-maleimidoethane; 3,3-dithiobis(sulfosuccinimidyl propionate); dthylene glycol bis(sulfosuccinimidylsuccinate); or dimethyl pimelimidate 2HCl.

7. A composition comprising the bivalent complex according to claim 1.

8. The composition according to claim 7, further comprising a pharmaceutically acceptable carrier.

9. The composition according to claim 7, wherein the distance between the gp120 binding molecules when attached to the flexible bivalent spacer/linker is in the range between 30 to 60 Å.

10. The composition according to claim 7, wherein the distance between the gp120 binding molecules when attached to the flexible bivalent spacer/linker is in the range between 50 to 55 Å.

11. The composition according to claim 7, wherein the gp120 binding molecule is a molecule that targets and binds to a "Phe43 cavity" on the trimeric HIV gp120 complex.

12. The composition according to claim 7, wherein the gp120 binding molecule is CD4M9, CD4M33, BMS 378806 or BMS488043.

13. The composition according to claim 12, wherein the flexible bivalent spacer/linker comprises tris(2-carboxyethyl) phosphine hydrochloride; tris-succinimidyl aminotriacetate; tris-(2-maleimidoethyl)amine; 5, 5'-Dithio-bis-(2-nitobenzoic acid); bis-[β-(4-zaidosalicylamido)ethyl]disulfide; 1,4-bis-maleimidobutane; 1,4-bis-maleimidyl-2,3-dihydroxybutane; bis-maleimidohexane; bis-maleimidoethane; 1,8-bis-maleimidotriethyleneglycol; 1,8-bis-(6-maleimidocaproylamido)-triethyleneglycol; 1,8-bis-[6-(4-N-maleimidomethyl-cyclohexane-1-carboxyl)amido]caproxyl-triethyleneglycol; 1,11-bis-maleimidotetraethyleneglycol; bis[2-(Succinimidyloxycarbonyloxy)-ethyl]sulfone; bis[Sulfosuccinimidyl]suberate; disuccinimidyl glutarate; dithiobis(succinimidyl propionate); disuccinimidyl suberate; dithio-bis-maleimidoethane; 3,3-dithiobis(sulfosuccinimidyl propionate); dthylene glycol bis(sulfosuccinimidylsuccinate); or dimethyl pimelimidate 2HCl.

14. The composition according to claim 13, further comprising an additional antiviral agent including nucleoside RT inhibitors, CCR5 inhibitors/antagonists or viral entry inhibitors.

15. A method of inhibiting entry of HIV into a cell, the method comprising: introducing an effective amount of a bivalent HIV inhibitor according to claim 1.

16. The method according to claim 15 wherein the distance between the gp120 binding molecules when attached to the flexible bivalent spacer/linker is in the range between 30 to 60 Å.

17. The method according to claim 15, wherein the distance between the gp120 binding molecules when attached to the flexible bivalent spacer/linker is in the range between 50 to 55 Å.

18. The method according to claim 15, wherein the gp120 binding molecule is a molecule that targets and binds to a "Phe43 cavity" on the trimeric HIV gp120 complex.

19. The method according to claim 15, wherein the gp120 binding molecule is CD4M9, CD4M33, BMS 378806 or BMS488043.

20. The method according to claim 19, wherein the flexible bivalent spacer/linker comprises tris(2-carboxyethyl)phosphine hydrochloride; tris-succinimidyl aminotriacetate; tris-(2-maleimidoethyl)amine; 5,5'-Dithio-bis-(2-nitobenzoic acid); bis-[β-(4-zaidosalicylamido)ethyl]disulfide; 1,4-bis-maleimidobutane; 1,4-bis-maleimidyl-2,3-dihydroxybutane; bis-maleimidohexane; bis-maleimidoethane; 1,8-bis-maleimidotriethyleneglycol; 1,8-bis-(6-maleimidocaproylamido)-triethyleneglycol; 1,8-bis-[6-(4-N-maleimidomethyl-cyclohexane-1-carboxyl)amido]caproxyl-triethyleneglycol; 1,11-bis-maleimidotetraethyleneglycol; bis[2-(Succinimidyloxycarbonyloxy)-ethyl]sulfone; bis[Sulfosuccinimidyl] suberate; disuccinimidyl glutarate; dithiobis(succinimidyl propionate); disuccinimidyl suberate; dithio-bis-maleimidoethane; 3,3-dithiobis(sulfosuccinimidyl propionate); dthylene glycol bis(sulfosuccinimidylsuccinate); or dimethyl pimelimidate 2HCl.

21. A method for detecting HIV infection in a biological sample, the method comprising:

contacting the biological sample with a bivalent HIV inhibitor according to claim 1; and detecting the formation of a gp120/bivalent inhibitor complex.

* * * * *

UNITED STATES PATENT AND TRADEMARK OFFICE
CERTIFICATE OF CORRECTION

PATENT NO. : 7,604,804 B2  Page 1 of 1
APPLICATION NO. : 11/054398
DATED : October 20, 2009
INVENTOR(S) : Wang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 183 days.

Signed and Sealed this

Fifth Day of October, 2010

David J. Kappos
*Director of the United States Patent and Trademark Office*

SEQUENCE LISTING

<160> NUMBER OF SEQ ID NOS: 2

<210> SEQ ID NO 1
<211> LENGTH: 28
<212> TYPE: PRT
<213> ORGANISM: Artificial Sequence
<220> FEATURE:
<223> OTHER INFORMATION: Synthetic construct

<400> SEQUENCE: 1

Cys Asn Leu Ala Arg Cys Gln Leu Arg Cys Lys Ser Leu Gly Leu Leu
1               5                   10                  15

-continued

```
Gly Lys Cys Ala Gly Ser Phe Cys Ala Cys Gly Pro
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic Construct
<220> FEATURE:
<221> NAME/KEY: X
<222> LOCATION: (1)..(1)
<223> OTHER INFORMATION: X = thiopropionic acid
<220> FEATURE:
<221> NAME/KEY: X
<222> LOCATION: (23)..(23)
<223> OTHER INFORMATION: X = biphenylalanine

<400> SEQUENCE: 2

Xaa Asn Leu His Phe Cys Gln Leu Arg Cys Lys Ser Leu Gly Leu Leu
1               5                   10                  15

Gly Lys Cys Ala Gly Ser Xaa Cys Ala Cys Val
            20                  25
```